(12) United States Patent
Cohen et al.

(10) Patent No.: US 10,835,172 B2
(45) Date of Patent: Nov. 17, 2020

(54) IMAGING DEVICE FOR ASSESSING SUNSCREEN COVERAGE

(71) Applicant: Voxelight, LLC, Raleigh, NC (US)

(72) Inventors: David S. Cohen, Chapel Hill, NC (US); Jonathan Meyer, Raleigh, NC (US); Wolfgang Wagner, Chapel Hill, NC (US); Connie Tran, Glen Allen, VA (US); Andrew Meyer, Raleigh, NC (US)

(73) Assignee: Voxelight, LLC, Raleigh, NC (US)

( * ) Notice: Subject to any disclaimer, the term of this patent is extended or adjusted under 35 U.S.C. 154(b) by 0 days.

(21) Appl. No.: 16/173,504

(22) Filed: Oct. 29, 2018

(65) Prior Publication Data

US 2019/0059805 A1 Feb. 28, 2019

Related U.S. Application Data

(63) Continuation of application No. PCT/US2017/029960, filed on Apr. 27, 2017.
(Continued)

(51) Int. Cl.
*H04N 7/18* (2006.01)
*A61B 5/00* (2006.01)
(Continued)

(52) U.S. Cl.
CPC ............ *A61B 5/441* (2013.01); *A61B 5/0077* (2013.01); *A61B 5/742* (2013.01); *G01N 21/33* (2013.01);
(Continued)

(58) Field of Classification Search
CPC ....... A61B 5/0077; A61B 5/441; A61B 5/472; G01J 1/0219; G01J 1/0233; G01J 1/429;
(Continued)

(56) References Cited

U.S. PATENT DOCUMENTS

| 8,965,460 B1 | 2/2015 | Rao et al. |
| 2006/0004306 A1* | 1/2006 | Altshuler ............. A61B 18/203 601/3 |

(Continued)

FOREIGN PATENT DOCUMENTS

JP 2014071007 A 4/2014

OTHER PUBLICATIONS

EPO, Search Report in European Application No. 17790478.6 dated Dec. 2, 2019.
(Continued)

*Primary Examiner* — Gims S Philippe
(74) *Attorney, Agent, or Firm* — NK Patent Law

(57) ABSTRACT

A device for assessing sunscreen coverage on a person includes a casing a lens assembly extending from about a front facing surface of the casing and allowing transmissivity to light energy in a wavelength range of about 300 to about 400 nm. A filter is in optical communication with the lens assembly and having a high optical density above about 390 nm and a low optical density below about 390 nm. A sensor is in optical communication with the filter, the sensor having a signal/noise ratio that is greater than about 36 db. A controller is configured for receiving input from a user to control the device. A display screen may be in communication with a controller for displaying an image associated with the filtered light.

15 Claims, 7 Drawing Sheets

Related U.S. Application Data

(60) Provisional application No. 62/385,326, filed on Sep. 9, 2016, provisional application No. 62/362,647, filed on Jul. 15, 2016, provisional application No. 62/353,563, filed on Jun. 23, 2016, provisional application No. 62/328,488, filed on Apr. 27, 2016.

(51) Int. Cl.
| | | |
|---|---|---|
| *G01N 21/33* | (2006.01) | |
| *G01N 21/84* | (2006.01) | |
| *G06T 7/00* | (2017.01) | |
| *H04N 5/225* | (2006.01) | |
| *G01N 21/21* | (2006.01) | |
| *G06T 7/90* | (2017.01) | |

(52) U.S. Cl.
CPC ....... *G01N 21/8422* (2013.01); *G06T 7/0012* (2013.01); *H04N 5/2254* (2013.01); *G01N 21/21* (2013.01); *G01N 2021/8427* (2013.01); *G06T 7/90* (2017.01); *G06T 2207/30088* (2013.01); *G06T 2207/30196* (2013.01)

(58) Field of Classification Search
CPC ... G01J 1/50; G01N 2021/8427; G01N 21/21; G01N 21/33; G01N 21/8422
USPC .......................................................... 348/158
See application file for complete search history.

(56) References Cited

U.S. PATENT DOCUMENTS

| | | | |
|---|---|---|---|
| 2006/0092315 | A1 | 5/2006 | Payonk et al. |
| 2006/0244961 | A1* | 11/2006 | Cole .................... A61B 5/0071 356/319 |
| 2008/0172047 | A1* | 7/2008 | Altshuler ............... A61B 5/441 606/9 |
| 2013/0300850 | A1 | 11/2013 | Millikan |
| 2014/0267882 | A1 | 9/2014 | O'Neill et al. |
| 2016/0025481 | A1 | 1/2016 | Stanfield et al. |
| 2016/0300471 | A1* | 10/2016 | Hwang .................. G01J 1/0219 |
| 2018/0202927 | A1* | 7/2018 | Isikman ................. G01N 33/00 |
| 2019/0078932 | A1* | 3/2019 | Simeone ................. H04L 67/12 |

OTHER PUBLICATIONS

WIPO; International Search Report for International Application No. PCT/US17/29960 dated Oct. 26, 2017.

WIPO; Written Opinion for International Application No. PCT/US17/29960 dated Oct. 26, 2017.

WIPO; International Preliminary Report on Patentability for International Application No. PCT/US17/29960 dated Oct. 30, 2018, 33 pages.

* cited by examiner

IMAGING DEVICE FOR ASSESSING SUNSCREEN COVERAGE

CROSS REFERENCE TO RELATED APPLICATIONS

This application is a continuation of international application no. PCT/US17/29960, filed on Apr. 27, 2017 entitled "IMAGING DEVICE FOR ASSESSING SUNSCREEN COVERAGE", which claims priority to US Provisional Patent Application Nos. 62/328,488 filed on Apr. 27, 2016 entitled "Device for Assessing Sunscreen Coverage," 62/353,563 filed on Jun. 23, 2016 entitled "Device for Assessing Sunscreen Coverage," 62/362,647 filed on Jul. 15, 2016 entitled "Device for Assessing Sunscreen Coverage," and 62/385,326 filed on Sep. 9, 2016 entitled "Device for Assessing Sunscreen Coverage", each of which is hereby incorporated by reference in its entirety.

TECHNICAL FIELD

This disclosure is related to an imaging device for assessing sunscreen coverage, and more particularly an imaging device for assessing sunscreen coverage by filtering light reflected off of a person wearing sunscreen to determine coverage thereof.

BACKGROUND

The fusion reactions in the Sun produce light energy across the whole electromagnetic spectrum from gamma rays through the tiny visible portion and beyond well into the infrared. Of particular concern to those who spend time outside are the ultraviolet portions of the spectrum which are invisible to us yet can cause severe burns to our skin and significantly increase our risk of developing cancers. The UV portion of the spectrum is typically divided into three sections—UVC, UVB & UVC. The wavelengths that correspond to those sections are: below 300 nm (UVC), 300-350 nm (UVB) & 350-400 nm (UVA). The oxygen and ozone in our atmosphere absorb much of the UVC radiation. However, the UVB and UVA rays pass through even clouds. As such, their impact to humans is significant.

Humans have developed myriad sunscreen creams and sprays to protect themselves from burns and skin damage caused by UVA and UVB radiation. These sunscreen products are highly effective when used properly yet most have been designed to completely disappear when rubbed into the skin. UVA & UVB are similarly invisible to humans. Therein presents a problem of how to assess how well one's sunscreen protection has either been applied or has fared after time and/or activity.

Disclosed herein is an improved device, method, and similar that allows for assessment of sunscreen coverage of a person.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter Disclosed herein is a device for assessing sunscreen coverage on a person includes a casing a lens assembly extending from about a front facing surface of the casing and allowing transmissivity to light energy in a wavelength range of about 300 to about 400 nm. A filter is in optical communication with the lens assembly and having a high optical density above about 390 nm and a low optical density below about 390 nm. A sensor is in optical communication with the filter, the sensor having a signal/noise ratio that is greater than about 36 db. A controller is configured for receiving input from a user to control the device. A display screen in communication with a controller for displaying an image associated with the filtered light.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings.

DETAILED DESCRIPTION

The presently disclosed invention is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies.

Figure 1:
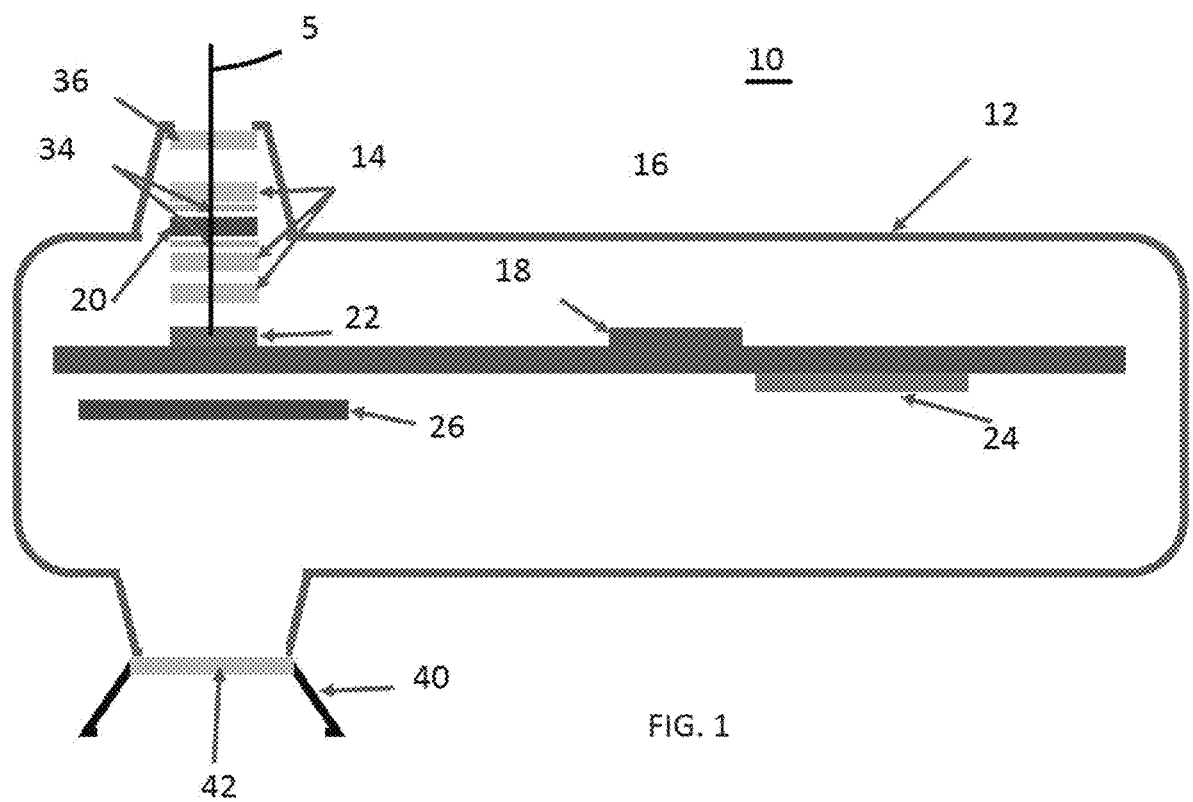
FIG. 1 illustrates one embodiment of a device and system disclosed herein.

FIG. 1 is a device for assessing sunscreen coverage on a person. The device is generally designated 10 and includes a casing 12. Casing 12 may be an injection molded multiple part assembly that is assembled together similar to the illustrated embodiment of FIG. 2, or casing 12 may take on any appropriately configured arrangement. A lens assembly 14 extending from about a front facing surface of the casing 12. As illustrated, a tapering protrusion may extend from a main body of the casing 12 to form a housing for receiving some of the lens assembly 14. The lens assembly 14 is shown as a stack of lenses, however, any appropriately configured amount of lenses may be provided and arranged as desired.

The lens assembly 14 is configured for allowing transmissivity to light energy in a wavelength range of about 300 to about 400 nm. More specifically, the lens assembly 14 may be configured for allowing transmissivity to light energy (illustrated with line 5 in the figures) up to any suitable range that is associated with UVA and UVB, such as, for example, up to 385 nm light energy, or above 280 nm light energy. Appropriate ranges for allowing transmissivity include for UVB, between 280 and 320 nm and for UVA, between 320 and 400 nm.

In one embodiment, the lens assembly 14 may include at least three lenses. The outermost lens is a meniscus type with aspheric surfaces. It has an outer diameter of 8 mm and a clear aperture of 3.5 mm. The second lens is a menicus type with aspheric surfaces. It has an outer diameter of 8 mm and a clear aperture of 3 mm. The third lens is a meniscus type with aspheric surfaces. It has an outer diameter of 8 mm and a clear aperture of 4.25 mm.

At least one lens of the lens assembly 14 may formed of a material selected from the group consisting of fused silica glass, borosilicate glass, fused quartz glass, soda lime glass, Magnesium fluoride glass, cyclic olefin copolymer, cyclic olefin polymer plastic, polymethylpentene plastic, silicone, and acrylic plastic. In one embodiment, the lens may be formed from cyclic olefin polymer plastic. A polarizer may be provided in communication with the lens assembly 14 in order to provide additional characteristics for the light for imaging purposes. The polarizer may be one of a Brewster window, a dichroic film, a dielectric film, a laminated film, a birefringent type, Wollaston type, a Glan-Thompson type, Rochon type, Glan-Taylor type, Glan-Laser type, a wire grid, a nanowire grid, a pixelated nanowire grid, a wave plate, or a beam splitter. In one or more embodiments, the lens assembly 14 is rotatable to allow viewing by another person while the display screen remains in view of the user.

A filter 20 is in optical communication with the lens assembly 14 and has a high optical density above about 390 nm and a low optical density below about 390 nm. As used herein, a high optical density may include a density above about at least 3 above 390 nm and a low optical density of about no more than 1 below about 390 nm.

A sensor 22 is in optical communication with the filter 20. The sensor 22 has a signal/noise ratio that is greater than about 36 db. In other embodiments, the signal/noise ratio may be greater than about 32 db. In other embodiments, the signal/noise ratio may be greater than about 40 db. The sensor 22 may be a CMOS, CCD or similar sensor. The sensor may be coated with materials that enhance sensitivity in the UV spectral range.

A controller 24 may be configured for receiving input from a user to control the device 10. The controller 24 may include a processor and be coupled with memory 18. The controller 24 may also be configured for executing computer control code configured for image manipulation, image storage and playback, and the like.

A display screen 26 is in communication with the controller 24 for displaying an image associated with the filtered light. Apertures 34 defined in the lens assembly 14 define the cone angle of the incoming light energy 5 for receipt through sensor 22 and onto display 26. The window 36 may also serve as an aperture in the lens system. A eye cup 40 and lens 42 may provide for ergonomic placement of a user's eye to view the image at display screen 26. The eye cup 40 has a shape and resiliency such that it can be temporarily folded back so as to facilitate use by persons wearing glasses. As illustrated with FIG. 2, the casing may define a recess for receiving a digit of an operator. In one or more embodiments, the display screen 26 is a screen of a mobile device, and the device 10 is configured for communicating with the mobile device to cause the mobile device to display the image on the display screen 26. The display screen may also be entirely external to the device 10, configured for communicating with the device and displaying an image on a screen. For example, device 10 could be used in a sunscreen spraying booth, a sunscreen coverage visualization booth or in communication with a commonly traveled area where visitors can image themselves to assess sunscreen coverage in a theme park or similar.

The controller 24 may be configured for receiving information associated with UV data at or near the time of imaging. The controller 24 may receive such information over a network 102 that is in communication with a remote server or servers 104. The UV data may, for example, be used by the controller to adjust the image to compensate for greater or less than ideal light exposure. The UV data may also be used by the controller to adjust a responsive element or elements within the lens to improve the performance of the lens. The UV data may also provide information related to amount of exposure that can be expected for a sunscreen application or for normalizing comparisons between images taken at subsequent times and thus in different UV scenarios. The controller 24 is further configured for storing the displayed images for review at a subsequent time. In this manner, a user can direct the controller 24 to view prior images of a subject. A profile associated with a subject may be enabled. For example, the images may be saved by the controller as "subject A" for one person, and "subject B" for another person. The controller 24 may then be configured to assess images associated with subject B. The controller 24 may also be configured to store information such as the provided UV data, time of taking an image, type of sunscreen and manner of application, and the like. The controller 24 may be further configured for providing an alarm indicative of a time that has passed since last use. The controller 24 may be in communication with a biometric or environmental sensor such as a UV radiometer or temperature sensor. The controller 24 may be configured to provide image enhancement for improved performance. For example, controller 24 may be configured to perform a transformation of the image for improved viewing performance on the display screen 26. In one or more embodiments, the controller 24 may be configured for causing to display sequential images taken at sequential times of a person. The controller 24 may be further configured to determine at least one characteristic relating to a change in the sequential images.

In one or more embodiments, the controller 24 recognizes regions of low and/or high sunscreen coverage on a person's skin and provides an additional visual indication on the display for those regions. For example, the additional visual indication may be, for example, a red colored zone provided on the display to signify an area of low sunscreen coverage. The visual indication may also be a blinking or other contrasted color. The visual indication on the display may employ two different colors, one to signify low sunscreen coverage and one to signify sufficient sunscreen coverage. Alternatively, multiple colors may be used to signify areas of low sunscreen coverage whereby a specific color corresponds to the UVA range and another color corresponds to the UVB range.

Figure 2:
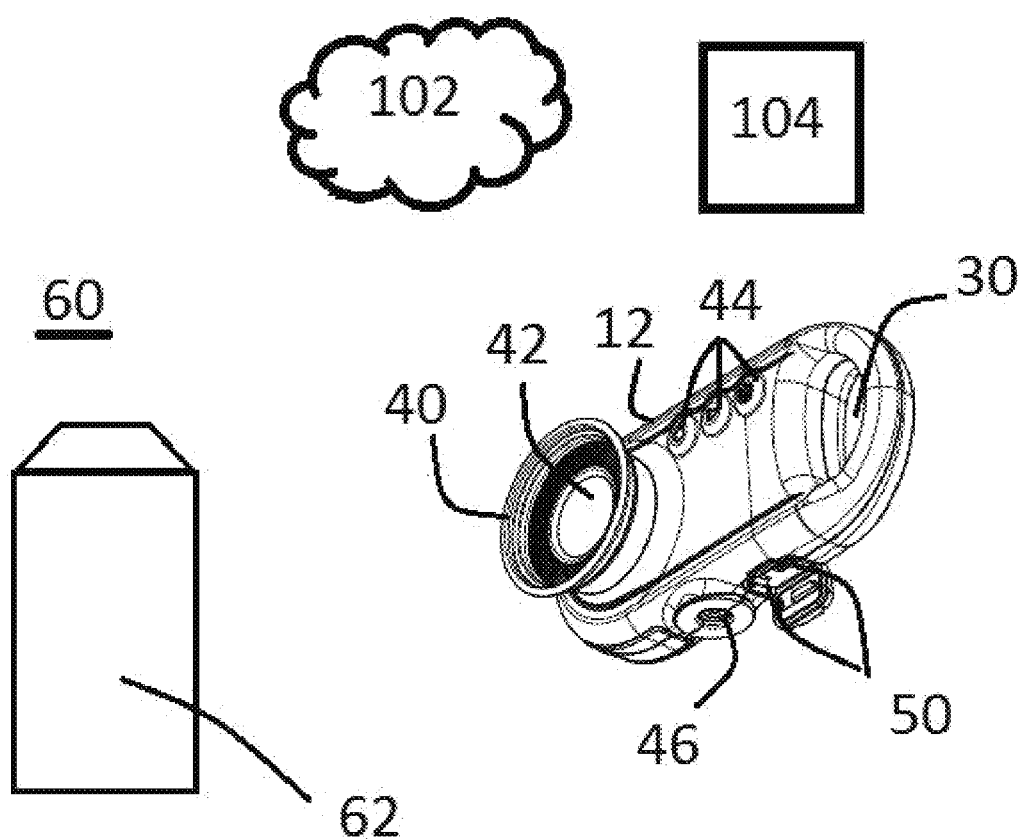
FIG. 2 illustrates one embodiment of a kit using any one of the devices and systems disclosed herein.

As illustrated in FIG. 2, the device 10 may include buttons 44 for being pressed by a user to manipulate controller 24. A mount 46 may be provided as a threaded recess for receiving, as one example, a tripod mount or similar. Input/output (IO) ports 50 may be provided for battery charging or passing of data. The passing of data through IO ports 50 may be accomplished through a wired connection that provides connectivity to an external storage or memory or other device such as a smart phone or mobile device, or a PC, or through network 102 to a remote server 104. Alternatively, device 10 may include wireless connectivity to network 102. As illustrated, the casing has a major dimension less than about five (5) inches.

As further illustrated in FIG. 2, the device 10 may be embodied as a kit 60 that includes a bottle of sunscreen 62 and device 10. In this manner, the device 10 may be provided and may be tuned to the type of sunscreen in the kit 60.

A method may be thus provided for using device 10. The method may include, for example, after sunscreen has been applied to a person, imaging the person with device 10. The method may further include causing to display an image of the imaged person, the image showing in contrast application of the sunscreen to the person. The method may further include additional applications of sunscreen and subsequent imaging to access areas of coverage.

Figure 3:
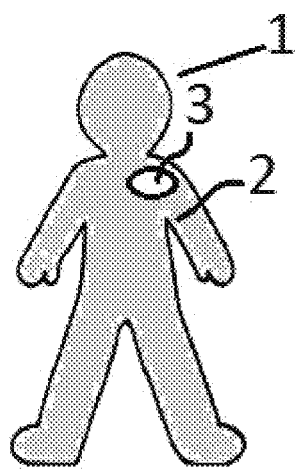
FIG. 3 illustrates an image formed by any one of the devices and systems disclosed herein.

An image for display to a user using the device 10 is illustrated in FIG. 3. The image 1 illustrates a subject that has appropriate coverage as indicated by 2, and insufficient coverage as indicated by 3. As already described, the area 3 may include contrasting colors, blinking, or other visual indicators.

Thus disclosed herein, in one embodiment, is an imaging lens is formed through the combination of one or more optical elements. Optical elements may include single lenses in any shape including, for example, freeform, meniscus, aspheric, bi-convex, bi-concave, plano-convex, plano-concave as well as apertures and filters. The spacing(s) between the elements is selected so as to optimize performance of the imaging lens. The filter is selected such that transmission is maximized in the region of the spectrum where sunscreen is maximally absorptive (300-400 nm) and transmission is minimized outside of that region (>400 nm). The placement of the filter with respect to the other optical elements is such that performance of both the lens system and the filter is optimal. The aperture(s) is are sized and placed with respect to the other optical elements is such that performance of both the lens system and the filter is optimal. The optical lens elements are, preferentially, formed of materials that provide maximal transmission in the region of the spectrum between 300 and 400 nm. Similarly, the coatings on the lens elements are selected so as to optimize performance of the lens elements in the region of the spectrum between 300 and 400 nm.

The imaging lens is mounted at a distance away from an imaging sensor (such as a CCD or CMOS) such that the image is formed with maximal resolution and focus on the plane of the image sensor. The image sensor is selected such that it has sufficient sensitivity in the UV region of the spectrum that a UV-only image can be produced by the sensor without the need for gain settings that would reduce image quality.

The image from the sensor may either be recorded or presented in a live feed via a screen mounted behind the camera board (see figure). A single or multi-element lens may be used to provide eye relief to the user such that when the user hold the device up to their eye the screen will appear to be in focus in a manner similar to a camera viewfinder.

In one or more embodiments, controller 24 may be configured, though sensor 22 or other components, to selectively display where UVA sunscreen coverage is provided on a subject and UVB sunscreen coverage is provided. In this manner, the user could press a button to display the UVA coverage, then a separate button for UVB coverage, and another button for combined coverage or the like.

Visualization of sunscreen on skin depends upon producing optical contrast between the areas where sunscreen absorbs UV light and areas where unprotected skin reflects UV light. Thus the preferred transmissivity range of the filter is the range that most closely aligns with the wavelength range of the ingredients used in sunscreen formulations. As will be appreciated by one skilled in the art, active ingredients in sunscreen formulations are regulated by bodies within governments and political unions such that sunscreen ingredients and formulations available in one country may not be available in another. Because of this, it may be necessary to produce various embodiments with the specifications of the optical filter tuned to more closely match the active ingredients that are available in a particular geographic region or country.

Most sunscreen formulations have ingredients that do not absorb much light energy above 390 nm, however the human eye does not see much light energy below 425 nm. An ingredient could be added to a sunscreen formulation that absorbs light energy in the range between 390 and 425 nm. An alternative embodiment of the device could have a filter with a transmissivity range that is includes up to 425 nm. This would enable visualization of any sunscreen formulation that included such an ingredient.

Visualization of sunscreen on skin depends upon producing optical contrast between the areas where sunscreen absorbs UV light and areas where unprotected skin reflects UV light. Visualization is confounded in instances where specular reflections from areas of skin that covered with sunscreen produce apparent bright spots. These bright areas can be misinterpreted as being unprotected skin when in fact they are merely an optical artefact. Light reflected from a non-metallic surface becomes polarized; this effect is maximum at Brewster's angle. Regardless of how the optical contrast is visualized (UV camera or lens-only) these bright spots can be reduced or eliminated by incorporation of a polarizing filter, element or functionality into the optical system that is rotationally aligned to be perpendicular the specular reflection light. The polarizer can be of any type provided that it intrinsically provides sufficient UV transmission to enable visualization of sunscreen. Examples of such suitable polarizers include but are not limited to: Brewster windows, dichroic films, laminated films, Wollaston, Glan-Thompson, Rochon, Glan-Taylor, Glan-Laser, wire grid, nanowire, pixelated, wave plates and beam splitters.

Alternatively, as described previously a conversion imaging approach may be employed to enable visualization of sunscreen on skin. This approach could be a lens-only system whereby no camera is employed for visualization or used in conjunction with a traditional camera such as a camera built into a smartphone. This approach employs a first lens assembly, a downconversion plate and a second lens assembly. The purpose of the downconversion plate is to convert UV to visible light. Prototyping efforts demonstrated that this approach is viable but produced images of limited resolution. It was observed that one of the significant contributors to the limitations on the resolution stemmed from the finite and inhomogeneous grain size of the downconversion material as well as the methodology used to form the layer of downconversion material. Development efforts has initially focused on sourcing downconversion materials with ever smaller grain sizes with even greater homogeneity and on improvement of processes for layer formation. These efforts yielded improvement in image quality but not sufficient enough to allow commercialization. It was then realized that causing the downconversion plate to move in one or two dimensions either rotationally, laterally or in a random or semi-random pattern could cause the inhomogeneities in the downconversion plate to apparently disappear due to blurring. The speed of the motion of the plate must be such that any single inhomogeneity would move to a degree that it would appear blurred even for the fastest time constant (shutter speed) of the visualization modality. For example, if a human were looking into the imaging system the plate would need to move fast enough and far enough such that the average size inhomogeneity in the plate would apparently disappear due the human "persistence of vision". The motion of the plate can be via rotation but the preferred embodiment is a linear or semi-random motion induced via a small piezoelectric transducer.

For all instances of visualization of sunscreen on skin it should be noted that all approaches could be built into or used in conjunction with a smartphone device. The smartphone device could be modified to include an extra camera for such purposes or modifications to standard smartphone cameras and/or software could be made. The lens-only conversion approach would be well suited to mounting on a smartphone to enable the standard camera in the smartphone to be used for visualization of sunscreen on skin.

Figure 4:
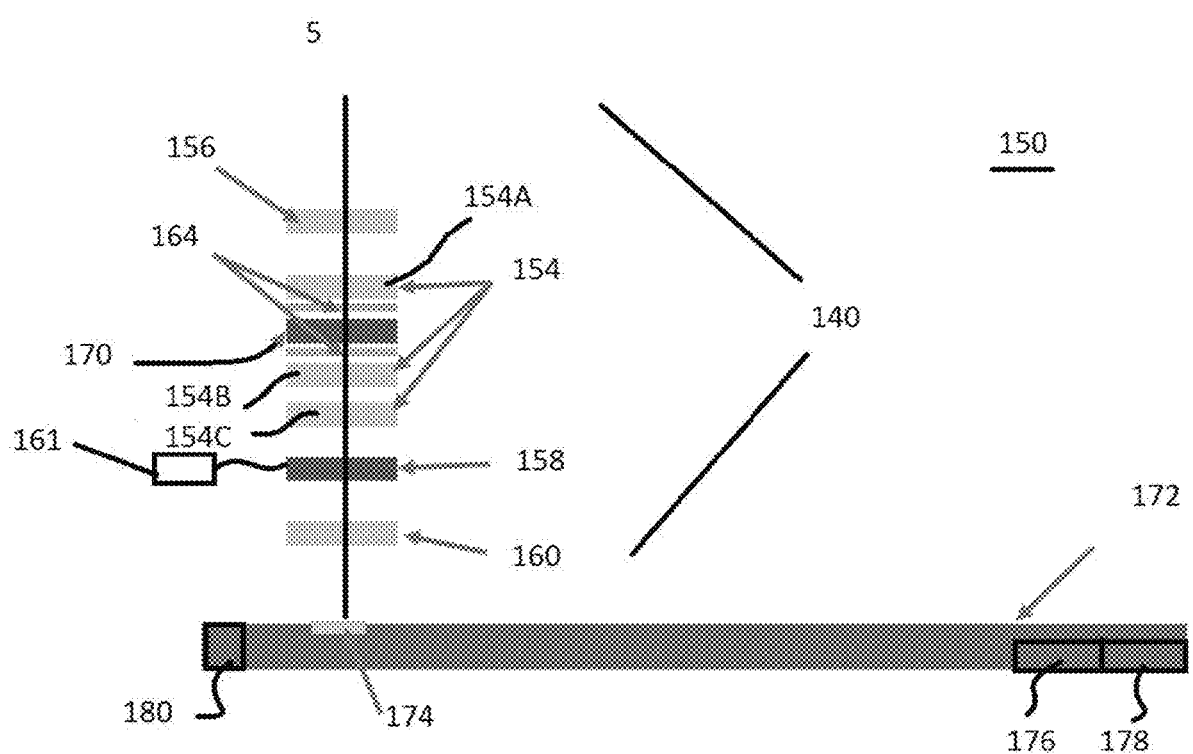
FIG. 4 illustrates one embodiment of a device and system disclosed herein.

One example of a stand-alone or separable lens approach is illustrated in FIG. 4. A device is generally designated 150 and is provided for assessing sunscreen coverage on a person. The device 150 may include a stack 140 that includes multiple components. For example, lens assembly 154 allows transmissivity to light energy in a wavelength range of about 300 to about 400 nm. Lens assembly 154 may share some characteristics with lens assembly 14. In one or more embodiments, the lens of the lens assembly 154 is formed of a material selected from the group consisting of fused silica glass, borosilicate glass, fused quartz glass, soda lime glass, Magnesium fluoride glass, cyclic olefin copolymer plastic, cyclic olefin polymer plastic, polymethylpentene plastic, silicone, and acrylic plastic. A filter 170 is in optical communication with the lens assembly and has a high optical density above about 390 nm and a low optical density below about 390 nm. A converter 158 converts ultraviolet light of the light energy into visible light. Apertures 164 and window 156 may be provided. A relay lens 160 conveys an image associated with the visible light. The light energy 5 and converted image is then conveyed to an imaging device 174, such as a camera, of mobile device 172. Mobile device 172 may further include a controller having a processor 176 and a memory 178 that stores computer control code. A radio 180 of the mobile device 172 may allow for communicating with an external entity.

Figure 5:
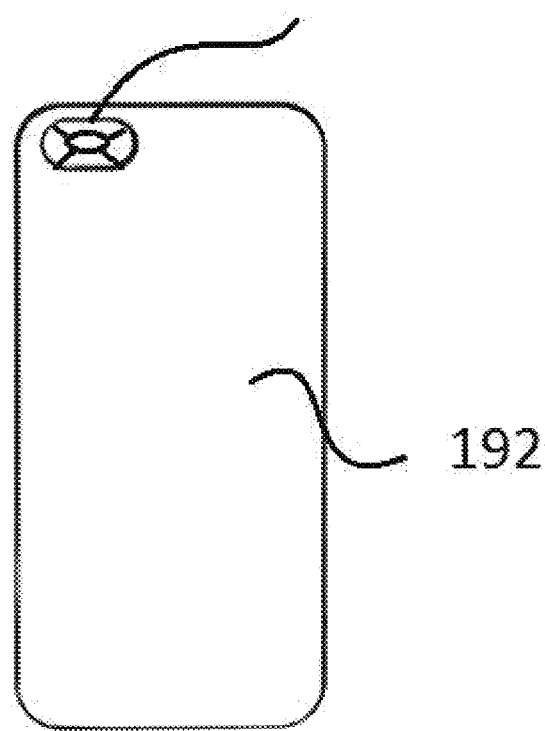
FIG. 5 illustrates an embodiment for an accessory for the device and system disclosed herein.

The stack assembly of lens 154, converter 158, relay 160, apertures 164, and the like may be embodied as a stand alone product appropriate for being viewed by a human eye or in combination with another external device. For example, the stack assembly may be further configured for being engaged with eyeglasses, a case for the mobile device, and the like. As illustrated in FIG. 5, the "stack", generally designated 190, may be embodied as an extension on a mobile device casing 192. The stack 190 may be slideable to define a position where the stack is inline with the imaging device/camera 174 or out of line to allow normal imaging. In other embodiments, the stack may be embodied entirely within the mobile device.

Figure 6:
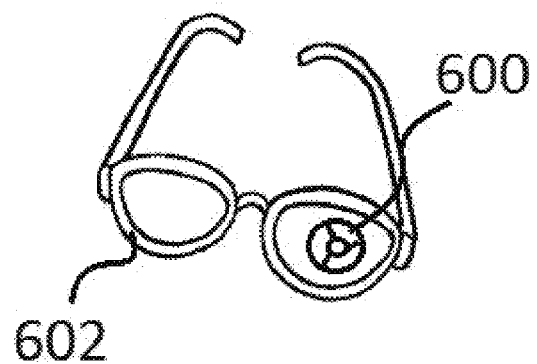
FIG. 6 illustrates an embodiment for an accessory for the device and system disclosed herein.

A similar arrangement is shown in FIG. 6, where the stack 600 is shown engaged with glasses 602.

The stack device 140 may be configured such that, when engaged with a mobile device, the relay lens 160 directs the light energy into the imaging device 174 of the mobile device 172. In one or more embodiments, the mobile device 172 includes a controller having a processor 176 configured for receiving information associated with UV data at or near the time of imaging. In one or more embodiments, the controller is further configured for storing images displayed on the mobile device for review at a subsequent time. In one or more embodiments, the controller is further configured for providing an alarm indicative of a time that has passed since last use. In one or more embodiments, the controller is in communication with a biometric or environmental sensor. In one or more embodiments, the controller performs image enhancement for improved performance. In one or more embodiments, the controller performs a transformation of the image for improved viewing performance on a display. In one or more embodiments, the controller recognizes regions of low and/or high sunscreen coverage on a person's skin and provides an additional visual indication on a display for those regions. In one or more embodiments, the visual indication is a blinking or contrasted color. In one or more embodiments, the controller is configured for causing to display sequential images taken at sequential times of a person. The controller is further configured to determine at least one characteristic relating to a change in the sequential images. In one or more embodiments, the controller is configured for storing the images for subsequent review. In one or more embodiments, the controller is in communication with a biometric, environmental, or UV dosage sensor.

Figure 7:
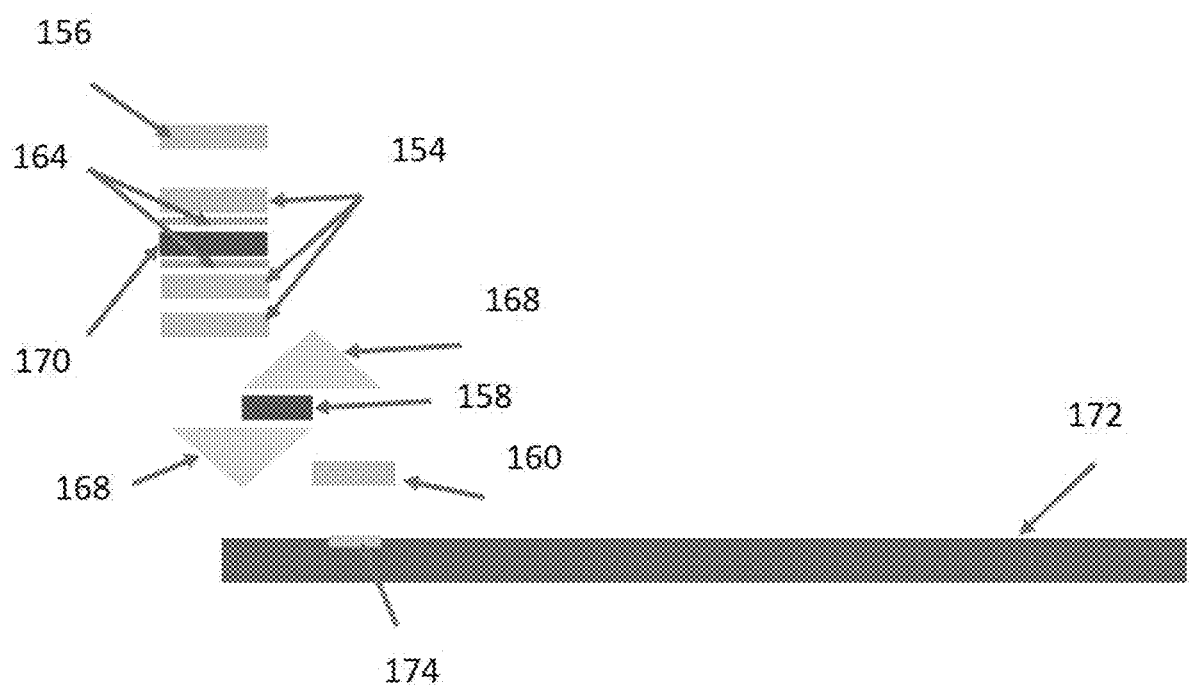
FIG. 7 illustrates one embodiment of a device and system disclosed herein.

In one or more embodiments, the device includes an imaging diverter 168 configured for re-directing the light energy. This diverter 168 is shown as a collection of prisms in FIG. 7. In alternate embodiments, the diverter 168 may be a mirror or multiple mirrors, or one of a prism with at least one mirrored surface or multiple prisms, each with at least one mirrored surface.

The lens assembly 154 may include a first lens 154A of a meniscus type with aspheric surfaces, a second lens 154B of a meniscus type with aspheric surfaces, and a third lens 154C of a meniscus type with aspheric surfaces.

In one or more embodiments, the first lens 154A has an outer diameter of between 7 and 72 mm, and a clear aperture of between 3 and 67 mm, the second lens 154B has an outer diameter of between 7 and 72 mm, and a clear aperture of between 2.5 and 66.5 mm, and the third lens has an outer diameter of between 7 and 72 mm, and a clear aperture of between 3.75 and 67.75 mm. A polarizer may be positioned along a light path of the light energy. The polarizer is one of a Brewster window, a dichroic film, a dielectric film, a laminated film, a birefringent type, Wollaston type, a Glan-Thompson type, Rochon type, Glan-Taylor type, Glan-Laser type, a wire grid, a nanowire grid, a pixelated nanowire grid, a wave plate, or a beam splitter.

The device according to claim 64, further including a manipulator 161 for moving the converter. The manipulator 161 may be one of a piezoelectric transducer, electric motor, coil driver, armature driver, orthodynamic driver, electrostatic driver, electret driver, magnetostrictive driver, or thermoacoustic driver. The manipulator 161 may be coupled to the converter.

Advantageously, the device, in some embodiments, produces an image that is viewable by a human eye.

The converter 158 can be provided and configured to produce two or more colors of visible light, one for light energy of a first type and one for light energy of a second type. Each color produced by the converter 158 may correspond with a specific region of the UV spectrum. The converter 158 may be an energy converting plate that is a fluorescent plate that converts the higher energy UV light into lower energy visible light viewable by the human eye. The energy converting plate may be an electronic sensor such as a CCD or a CMOS sensor. The ultraviolet light is converted to visible light to a secondary electronic screen such as an LCD screen or an OLED screen. The fluorescent plate may be configured to produce two or more colors of visible light, with each color corresponding to a specific region of the UV spectrum.

In one or more embodiments, the first lens 154A has an outer diameter of between 7 and 104 mm, and a clear aperture of between 3 and 99 mm. In one or more embodiments, the second lens 154B has an outer diameter of between 7 and 104 mm, and a clear aperture of between 2.5 and 98.5 mm. In one or more embodiments, the third lens has an outer diameter of between 7 and 104 mm, and a clear aperture of between 3.75 and 99.75 mm.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like conventional procedural programming languages, such as the "C" programming language or similar programming languages, and hardware description languages such as VHDL and Verilog or the like. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A device for assessing sunscreen coverage on a person, the device comprising:
    a casing;
    a lens assembly extending from about a front facing surface of the casing and allowing transmissivity to light energy in a wavelength range of 300 to 400 nm, the lens assembly including at least a first lens and a second lens in a light path,
    wherein the lens of the lens assembly is formed of a material selected from the group consisting of fused silica glass, borosilicate glass, fused quartz glass, soda lime glass, Magnesium fluoride glass, cyclic olefin copolymer plastic, cyclic olefin polymer plastic, polymethylpentene plastic, silicone, and acrylic plastic;

a filter in optical communication with the lens assembly and having a high optical density above 390 nm and a low optical density below 390 nm, the filter positioned in the light path between the first lens and the second lens;

a sensor in optical communication with the filter, the sensor having a signal/noise ratio that is greater than 36 db;

a controller configured for receiving input from a user to control the device;

a display screen in communication with a controller for displaying an image associated with the filtered light.

2. The device according to claim 1, wherein the casing defines a recess for receiving a digit of an operator.

3. The device according to claim 1, further comprising a polarizer within the light path of the light energy.

4. The device according to claim 3, wherein the polarizer is one of a Brewster window, a dichroic film, a dielectric film, a laminated film, a birefringent type, Wollaston type, a Glan-Thompson type, Rochon type, Glan-Taylor type, Glan-Laser type, a wire grid, a nanowire grid, a pixelated nanowire grid, a wave plate, or a beam splitter.

5. The device according to claim 1, wherein the controller is further configured for receiving information associated with UV data at or near the time of imaging.

6. The device according to claim 1, wherein the controller is further configured for storing the displayed images for review at a subsequent time.

7. The device according to claim 1, wherein the controller is further configured for providing an alarm indicative of a time that has passed since last use.

8. The device according to claim 1, wherein the controller is in communication with a biometric or environmental sensor.

9. The device according to claim 1, wherein the controller performs a transformation of the image for improved viewing performance on the display.

10. The device according to claim 1, wherein the controller recognizes regions of low and/or high sunscreen coverage on a person's skin and provides an additional visual indication on the display for those regions.

11. The device according to claim 1, wherein the controller is configured for causing to display sequential images taken at sequential times of a person, wherein the controller is further configured to determine at least one characteristic relating to a change in the sequential images.

12. The device according to claim 1, wherein the display screen is a screen of a mobile device, and the device is configured for communicating with the mobile device to cause the mobile device to display the image on the display screen.

13. The device according to claim 1, wherein the display screen is a screen external to the casing.

14. A method of imaging a person to which sunscreen has been applied, the method comprising:

imaging the person to which the sunscreen has been applied with a device, the device including a lens assembly allowing transmissivity to light energy in a wavelength range of 300 to 425 nm, a filter having a high optical density above 390 nm and a low optical density below 390 nm, and a sensor in optical communication with the filter, the sensor having a signal/noise ratio that is greater than 36 db; and displaying an image of the imaged person, the image showing in contrast application of the sunscreen to the person, wherein the lens assembly includes at least a first lens and a second lens in a light path, and wherein the filter is positioned in the light path between the first lens and the second lens.

15. The method according to claim 14, wherein the device has a casing that defines a recess for receiving a digit of an operator, the method further including positioning of an operator's digit within the recess.

* * * * *